United States Patent [19] [11] 3,936,508
Wenzel et al. [45] Feb. 3, 1976

[54] PROCESS FOR THE PREPARATION OF CHLOROPRENE

[75] Inventors: Rupert Wenzel; Gerhard Scharfe, both of Leverkusen, Germany

[73] Assignee: Bayer Aktiengesellschaft, Germany

[22] Filed: Feb. 27, 1974

[21] Appl. No.: 446,495

[30] Foreign Application Priority Data
Mar. 3, 1973 Germany............................ 2310744

[52] U.S. Cl.............................. 260/655; 260/654 D
[51] Int. Cl.$^2$.................. C07C 17/34; C07C 21/21
[58] Field of Search........................ 260/655, 654 D

[56] References Cited
UNITED STATES PATENTS
2,542,976   2/1951   Airs et al. ........................ 260/654 D FOREIGN PATENTS OR APPLICATIONS
42-25054   11/1967   Japan................................. 260/655
1,055,064   1/1967   United Kingdom................. 260/655

Primary Examiner—D. Horwitz
Attorney, Agent, or Firm—Connolly and Hutz

[57] ABSTRACT

A process for producing chloroprene from 3,4-dichlorobutene-1 and sodium hydroxide solution wherein a dehydrated mixture of n-butanol and aqueous sodium hydroxide solution is reacted with 3,4-dichlorobutene-1 to form chloroprene and solid sodium chloride.

5 Claims, 1 Drawing Figure

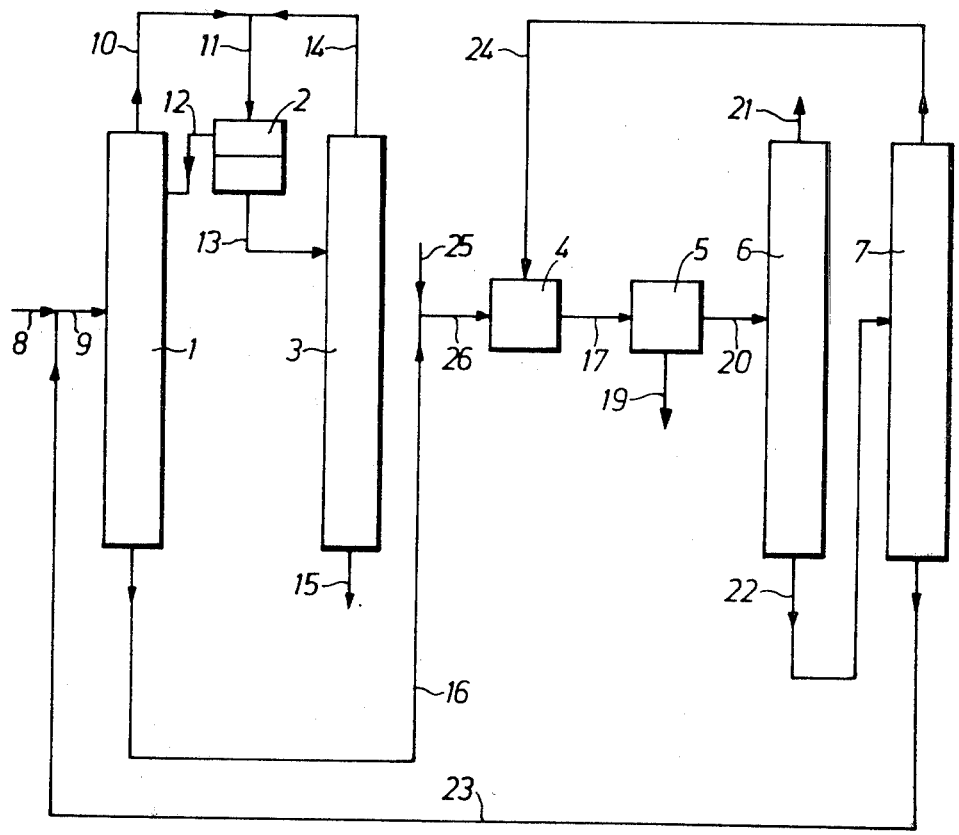

PROCESS FOR THE PREPARATION OF CHLOROPRENE

This invention relates to a process for the preparation of 2-chlorobutadiene-1,3 (chloroprene) by the action of substances which split off hydrogen chloride on 3,4-dichlorobutene-1 in the presence of organic solvents.

U.S. Pat. No. 2,180,115 discloses the reaction of 1,2-dihalobutene with an alkaline reagent in the presence of an organic solvent at the boiling point of the solvent to produce a β-halobutadiene. Thus for example 3,4-dichlorobutene-1 may be converted to chloroprene by this method. The following alkaline reagents may be used: sodium methoxide, potassium methoxide, potassium ethoxide, pyridine, quinoline, triethanolamine and suspensions of sodium carbonate or potassium carbonate.

U.S. Pat. No. 2,430,016 describes a process in which chloroprene is obtained by reacting 1,2-dichlorobutene-3 with aqueous solutions of sodium hydroxide. This process is said to have advantages over the process of U.S. Pat. No. 2,180,115 as using aqueous solutions of sodium hydroxide increases the yield of chloroprene and renders the process more economical and simpler. In particular the chloroprene need not be recovered from mixtures containing organic solvents.

In the process of U.S. Pat. No. 2,180,115 1 mol of methanol or ethanol is formed as a by-product, when 1 mol of 1,2-dichlorobutene-3 is reacted with sodium methoxide or sodium ethoxide. It turned out that the chloroprene cannot be separated from the methanol or ethanol by fractional distillation as hitherto unknown azeotropic mixtures are formed, i.e. an azeotropic mixture of chloroprene and 25 % of methanol, boiling at 49°C or an azeotropic mixture of chloroprene and 15 % of ethanol, boiling at 55°C. Therefore more involved methods have to be used to recover pure chloroprene.

U.S. Pat. No. 3,639,492 relates to a process for producing chloroprene by reacting 3,4-dichlorobutene-1 with an aqueous sodium hydroxide solution in the presence of 0.1 to 15 % by weight (based on dichlorobutene) of certain sulfonium compounds. Such compounds may be made, e.g. by reacting dodecyl-2-hydroxy-ethyl-sulphide and methyl iodide. This additive accelerates the reaction so that the disadvantages of the process of U.S. Pat. No. 2,430,016 are overcome.

The processes according to U.S. Pat. Nos. 2,430,016 and 3,639,492 use inexpensive aqueous sodium hydroxide solutions as starting materials and 3,4-dichlorbutene-1. However, 1 mol of sodium chloride as a dilute aqueous solution is obtained per mol of chloroprene.

The discharge of this aqueous sodium chloride solution as waste water presents a serious water pollution problem on account of its salt content and/or its content of organic compounds such as organic chlorocompounds. Thus there is a demand of a process for producing chloroprene in which the advantages of using aqueous sodium hydroxide solutions are preserved but in which no waste water containing sodium chloride is formed.

It has now been found that the disadvantages of the known processes for producing chloroprene by subjecting 3,4-dichlorobutene-1 to the action of substances which split off hydrogen chloride can be obviated as follows: An aqueous solution of sodium hydroxide and n-butanol is dehydrated by azeotropic distillation in a first distillation column to form effluent water which is practically free from organic constituents by removing from the head of the column a binary mixture of n-butanol and water, condensing the mixture and separating it into layers in a separator and then returning the upper (n-butanol-rich) phase to the distillation process and introducing the lower (aqueous) phase into a second distillation column where it is stripped from dissolved n-butanol, the head product from the second column being then returned to the head product of the first column so that pure effluent water is obtained in the sump of the second column. The sump from the first column which is completely water-free and constitutes essentially sodium butylate dissolved in n-butanol is then reacted with 3,4-dichlorobutene-1 in the liquid phase at temperatures of 0° to 200°C in the absence of molecular oxygen. The solid sodium chloride formed in this reaction is mechanically removed from the reaction mixture while the chloroprene formed in the reaction is isolated by distillation in a third distillation column. The liquid residue, which consists mainly of n-butanol, is then introduced into a fourth distillation column where it is freed from unreacted 3,4-dichlorobutene-1 by removing from the head of the column an azeotropic mixture of 3,4-dichlorobutene-1 and n-butanol which contains about 50 % of 3,4-dichlorobutene-1 and boils at 113°C and returning this azeotropic mixture to the reaction of 3,4-dichlorobutene-1 with the sump product from the first distillation column. At the same time, the sump product from the fourth distillation column is returned to the first distillation column.

The process according to the invention has the following advantages: The reaction of 3,4-dichlorobutene-1 with the sump product from the first distillation column takes place in a homogeneous phase. Chloroprene can easily be obtained in a pure form from the reaction product by fractional distillation since it does not form an azeotropic mixture with n-butanol. Sodium chloride which is formed in the reaction is insoluble in the reaction product and can be removed mechanically, e.g. by filtration or centrifuging, and can be obtained in an anhydrous form. No effluent water containing sodium chloride and/or organic compounds is obtained.

The reaction of 3,4-dichlorobutene-1 with sump product from the first distillation column is advantageously carried out in the absence of oxygen. When carrying out the distillation in the first column, any molecular oxygen dissolved in the aqueous sodium hydroxide solution is removed by stripping. The reaction of 3,4-dichlorobutene-1 and recovery of chloroprene by distillation may be carried out in the presence of inhibitors.

Chloroprene is an important monomer for the production of polychloroprene rubbers.

The reaction of 3,4-dichlorobutene-1 with the sump product from the first distillation column may be carried out at temperatures of 0° to 200°C, e.g. at 50° to 150°C. It may be carried out at atmospheric, superatmospheric or subatmospheric pressure. The first column may be operated with a ratio of 1 mol of 3,4-dichlorobutene-1 to 1 mol of sodium in the sump product although other ratios may also be employed, for example 1.0 to 1.1 mol of 3,4-dichlorobutene-1 per mol of sodium in the sump product of the first column.

The sodium compounds present in the sump product of the first column can be converted practically completely into insoluble chloride. The conversion of 3,4-dichlorobutene-1 to chloroprene is in the order of 90 to 100 %. The process may be carried out in such a manner that after the reaction and separation of the sodium chloride and chloroprene a liquid product is left which consists mainly of n-butanol and may contain small quantities of unreacted 3,4-dichlorobutene-1. After removal of any 3,4-dichlorobutene-1 which may be present in the fourth distillation column, a liquid product consisting mainly of n-butanol is left. If desired, a part of this liquid product may be purified by redistillation, e.g., in a thin layer evaporator, before its return to the first column, so that contaminants, such as high boiling side products do not accumulate therein.

The residence time of the reactants in the reaction of the sump product of the first distillation column and 3,4-dichlorobutene-1 may vary within wide limits, for example from 1 to 60 minutes, preferably 5 to 20 minutes. Various types of reactors are suitable, for example stirrer vessels and reaction tubes. The reaction may be carried out isothermally, adiabatically in partly adiabatically. It may be carried out at or near the boiling point of butanol. The heat of reaction may be used to evaporate the chloroprene formed in the reaction and optionally part of the n-butanol. The vapours which consist mainly of chloroprene and n-butanol and possibly unreacted 3,4-dichlorobutene-1 may be separated in a distillation column, chloroprene being obtained as head product.

The reaction temperature and/or reaction pressure employed for the conversion of 3,4-dichlorobutene-1 to chloroprene may also be below the boiling point of the mixture of chloroprene/n-butanol/3,4-dichlorobutene-1. Then no vapours containing chloroprene leave the reactor. For example, the mixture of sump product from the first column and 3,4-dichlorobutene-1 may be passed upwardly through a reaction tube at a pressure of 5 atmospheres and an inlet temperature of 60°C. Due to a favourable distribution of residence times under these conditions, the sodium compounds in the sump product from the first distillation column are completely converted to sodium chloride. If the flow velocity is made higher than the sedimentation velocity of the sodium chloride formed, the reaction mixture, which consists of chloroprene, unreacted 3,4-dichlorobutene-1, n-butanol and suspended sodium chloride, may be transferred directly to a device for the mechanical separation of sodium chloride, e.g., a decanter. After removal of the sodium chloride, the chloroprene can be recovered from the reaction mixture in a distillation column. It has surprisingly been found that when this method is employed no losses due to polymerisation of chloroprene occur.

The mechanically separated sodium chloride may, if necessary, be freed from any impurities present by washing it with pure butanol. The n-butanol used as washing liquid can be recovered in pure form as a side stream from the lower part of the first distillation colum. Very pure sodium chloride can be obtained in known manner by drying with recovery of the n-butanol contained in it and may then be used for other purposes, e.g. for electrolysis. The n-butanol recovered from the sodium chloride in the drying step may be returned to the first distillation column. The aqueous sodium hydroxide required for the reaction may contain differing quantities of sodium hydroxide. A commercial concentrated solution of sodium hydroxide in water containing e.g. 50 % by weight of sodium hydroxide may be used. The n-butanol is generally used in quantities of 2 to 10 mol, preferably 3 to 7 mol per mol of sodium hydroxide.

EXAMPLE

The method of carrying out the example is described with reference to the FIGURE. 564 g per hour of soda lye containing 282 g of sodium hydroxide and 3,140 g per hour of a return stream 23 consisting of n-butanol are introduced into a first distillation column 1 from pipe 9. A binary mixture of n-butanol and water is removed from the head of the column 1 at 10 and after cooling it is introduced by way of 11 into the separator 2 in which it is separated into layers. The upper phase is returned to 1 by way of 12. The lower phase is introduced into a second distillation column 3 by way of 13. In this distillation column 3, the dissolved n-butanol is removed at the head as a binary mixture with water and returned to 2 by way of 14 and 11. Pure water is removed from the sump of the column 3 at 15 at the rate of 409 g per hour. The sump from column 1 discharged through pipe 16 and 883 g of 3,4-dichlorobutene-1 from 25 are together introduced at 26 into a stirrer vessel 4 in which practically complete conversion of dichlorobutene to sodium chloride and chloroprene takes place with a residence time of 1 hour at 60°C. The reaction product is carried by way of 17 to the decanter 5 where the sodium chloride is separated mechanically and removed through pipe 19. The n-butanol recovered when the sodium chloride is subsequently dried is returned to 5. The reaction product freed from sodium chloride is introduced into the third distillation column 6 by way of 20. In this distillation column 6, chloroprene is removed as head product at 21 at the rate of 625 g per hour. The sump from column 6 is introduced into a fourth distillation column 7 by way of 22. In this fourth column 7, a head product is removed at the rate of 5%, based on the rate of flow from 22, and this head product is returned to 4 by way of pipe 24. The sump from column 7 is returned to the first distillation column 1 by way of pipe 23.

We claim:

1. A process for producing chloroprene which comprises dehydrating a mixture of an aqueous alkali metal hydroxide solution and n-butanol by azeotropic distillation, then reacting resulting dehydrated mixture with 3,4-dichlorobutene-1, removing insoluble alkali metal chloride from resulting reaction mixture and distilling resulting liquid reaction product to separate chloroprene and n-butanol.

2. The process of claim 1 wherein said reaction is carried out at a temperature of from 0° to 200°C.

3. The process of claim 1 wherein said alkali metal hydroxide is sodium hydroxide.

4. The process of claim 1 wherein said reaction is carried out in the substantial absence of oxygen.

5. The process of claim 1 wherein the reaction is carried out at a temperature and at a pressure at which chloroprene is liquid.

* * * * *